United States Patent [19]

Wang et al.

[11] 4,391,755
[45] Jul. 5, 1983

[54] STEROID MONOHYDRATES, FORMULATIONS CONTAINING SAME AND METHOD

[75] Inventors: Yu-Chang J. Wang, North Brunswick; Dürsch Friedrich, Hopewell; Richard L. O'Laughlin, North Brunswick; Thaddeus Prusik, Roosevelt, all of N.J.

[73] Assignee: E. R. Squibb & Sons, Inc., Princeton, N.J.

[21] Appl. No.: 340,127

[22] Filed: Jan. 18, 1982

[51] Int. Cl.³ .................... C07J 5/00; A61K 31/56
[52] U.S. Cl. .......................... 260/397.45; 424/243
[58] Field of Search .................... 260/397.45; 424/243

[56] References Cited

U.S. PATENT DOCUMENTS 3,937,720 2/1976 Varmi et al. .................... 260/397.45

OTHER PUBLICATIONS

Collard, R. E., "Formulation and Manufacture of Corticosteroid Preparations" (1961), *Pharm. J.*, 186, 113–117.
Carless, et al. "Dissolution and Crystal Growth in Aqueous Suspensions of Cortisone Acetate", *J. Pharm. Pharmac,* 1968 20, 630–638.
Carless, et al., "Effect of Crystal Form, Cortisone Alcohol and Agitation on Crystal Growth of Cortisone Acetate in Aqueous Suspensions", *J. Pharm. Pharmac.* 1968, 20, 639–645.

*Primary Examiner*—Elbert L. Roberts
*Attorney, Agent, or Firm*—Lawrence S. Levinson; Burton Rodney

[57] ABSTRACT

A monohydrate of a steroid having the structure

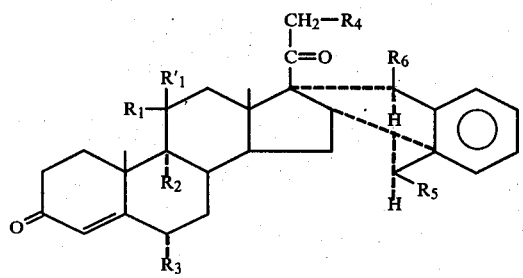

and the 1,2-dehydro derivatives thereof, is provided which monohydrate is in the form of a particulate material having a stable average particle size of less than about 20 microns. Cream and lotion formulations containing the steroid monohydrate and a method for forming the monohydrate are also provided.

14 Claims, No Drawings

STEROID MONOHYDRATES, FORMULATIONS CONTAINING SAME AND METHOD

FIELD OF THE INVENTION

The present invention relates to steroid monohydrates which have stable particle sizes, to creams, lotions and other water-containing formulations containing such steroid monohydrates and to a method for making such steroid monohydrates.

BACKGROUND OF THE INVENTION

It is known that cortisone acetate exists in several polymorphic forms. Collard, R. E. (1961), *Pharm. J.*, 186, 113–117 published photographs of $4\mu$ particles of cortisone acetate which changed to particles of up to $100\mu$ by suspension in water for less than 24 hours. Carless, et al., "Dissolution and crystal growth in aqueous suspensions of cortisone acetate", *J. Pharm. Pharmac.*, 1968, 20, 630–638, describe a technique for limiting crystal growth of cortisone acetate by mixing 100 mg micronized cortisone acetate with 0.5 ml of 5% v/v solution of Nonidet P42 (Shell Oil Co. non-ionic wetting agent which has approximately 27% of a polyethylene oxide condensate as active material) in 0.9% w/v solution of sodium chloride. This was then gradually diluted with 9.5 ml of the Nonidet-sodium chloride solution. The cortisone acetate changes to the water stable form with very little change in size distribution, Carless, et al. "Effect of crystal form, cortisone alcohol and agitation on crystal growth of cortisone acetate in aqueous suspensions", *J. Pharm. Pharmac.*, 1968, 20, 639–645.

U.S. Pat. No. 3,937,720 to Varma, et al. discloses steroids of the general structure

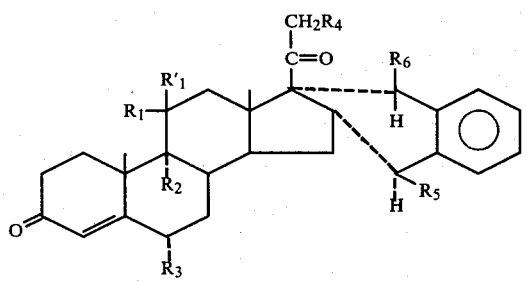

and the 1,2-dehydro derivatives thereof, wherein $R_1$ is chlorine, fluorine, or hydroxy and $R'_1$ is hydrogen or $R_1$ and $R'_1$ together are =O; $R_2$ is hydrogen or halogen; $R_3$ is hydrogen, methyl, or fluorine; $R_4$ is hydrogen, hydroxy,

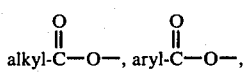

or halogen; $R_5$ and $R_6$ are the same or different and are hydrogen, alkyl, alkylthio, alkoxy, carboalkoxy, formyl,

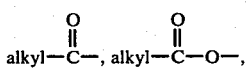

hydroxy, halogen, phenyl or cyano, with the proviso that when $R_5$ and $R_6$ are different, one of $R_5$ and $R_6$ is hydrogen, included within the above are 21-(acetyloxy)-9-fluoro 1',2',3',4'-tetrahydro-11β-hydroxypregna-1,4-dieno-[16α,17-b]naphthalene-3,20-dione and (11β,16β)-9-fluoro-1',2',3',4'-tetrahydro-11,21-dihydroxypregna-1,4-dieno[16,17-b]naphthalene-3,20-dione.

It has been found that steroids as defined herein when micronized and suspended in water undergo a transformation to their monohydrate form within several hours with a concomitant increase in particle size. In fact, the micronized particles upon hydration grow from an average particle size of less than 20 microns and usually less than 10 microns into long needle-like crystals about 50 to 75 microns in length. These long crystals are undesirable because their smaller surface area may reduce dissolution rate and bioavailability.

DESCRIPTION OF THE INVENTION

In accordance with the present invention, there is provided a steroid in the form of its monohydrate which has a stable average particle size of less than about 20 microns and has a dissolution rate and bioavailability equivalent to the steroid in its anhydrous form.

The steroid monohydrate of the invention is a monohydrate of a steroid having the structure

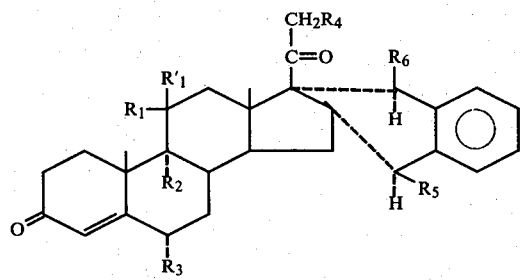

and the 1,2-dehydro derivative thereof, wherein $R_1$ is chlorine, fluorine or hydroxy and $R'_1$ is hydrogen or $R_1$ and $R'_1$ together are =O; $R_2$ is hydrogen or halogen; $R_3$ is hydrogen, methyl or fluorine; $R_4$ is hydrogen, hydroxy,

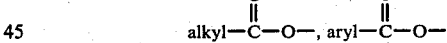

or halogen; and $R_5$ and $R_6$ are the same or different and are hydrogen, alkyl, alkylthio, alkoxy, carboalkoxy, formyl,

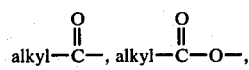

hydroxy, halogen, phenyl or cyano, with the proviso that when $R_5$ and $R_6$ are different, one of $R_5$ and $R_6$ is hydrogen.

The above steroids are disclosed in and prepared as described in U.S. Pat. No. 3,937,720 which is incorporated herein by reference.

In addition, in accordance with the present invention, a method is provided for forming the steroid monohydrate of stable particle size as described above, which method includes the steps of micronizing the steroid, in anhydrous form, to reduce average particle size to below about 20 microns, preferably below about 10 microns and optimally below about 5 microns, introducing the micronized anhydrous steroid into water to form a suspension containing for about 5 to about 20% by weight steroid and preferably from about 10 to about 15% by weight steroid, and allowing the steroid to remain in suspension for a minimal period of 0.1 hour and preferably from about 0.5 to about 4 hours, to thereby form the monohydrate of the steroid in the form of long needle-like crystals having an average length greater than 40 to 50 microns or more, reducing the average particle size of the monohydrate crystals, for example, by passing the suspension through a high energy colloid mill, to below about 25 microns, to preferably below about 10 microns, and optimally below about 5 microns, to produce the steroid monohydrate in a form having a stable crystal size. Furthermore, emulsification of the aqueous suspension of such monohydrate with other excipients as described hereinafter results in a cream or lotion wherein the steroid monohydrate will experience no further crystal growth.

The high energy colloid mill or similar apparatus employed in reducing the average particle size of the monohydrate crystals will preferably be of the impact type, that is a stream of the aqueous suspension of the steroid monohydrate will be impacted against a static plate under high pressures of 5000 psi or more. Grinding mechanisms, ball mills, homomixer, and hand homogenizers are not effective in breaking the suspended hydrate particles.

An alternative method for forming the steroid monohydrate is also provided, which method includes the steps of micronizing the steroid, in anhydrous form, to reduce average particle size to below about 20 microns, preferably below about 10 microns and optimally below about 5 microns, subjecting the micronized anhydrous steroid to a relative humidity of higher than about 40%, and preferably higher than about 80%, for a period of at least about 4 hours, and preferably at least about 24 hours to form a monohydrate having a crystal size and shape which remains in the desirable range during this hydration from the vapour phase; no further comminution is required.

One embodiment of the above alternative method, which is a preferred embodiment, includes the steps of forming a thin layer of the micronized anhydrous steroid (such as less than 1 cm) such as on a tray or other flat surface, providing one, two or more beakers of water in the vicinity of the layer of steroid, enclosing the atmosphere surrounding the steroid and beakers such as with a piece of plastic or plastic bag, and allowing the assembly to remain for at least ½ day and preferably at least 1 day, preferably at ambient temperature, to thereby form the steroid monohydrate without any growth in particle size.

The steroid monohydrate so-produced having a stable crystal size may be incorporated into a cream or lotion vehicle without any further crystal growth.

Furthermore, in accordance with the present invention, cream and lotion steroid formulations are provided wherein a steroid monohydrate having a stable average particle size of less than about 20 microns, preferably less than about 10 microns, and optimally less than about 5 microns is included.

The steroid monohydrate will be present in an amount of from about 0.001 to about 3% by weight, and preferably from about 0.025 to about 0.2% based on the total weight of the composition, depending upon the steroid monohydrate employed and its solubility in the vehicle employed.

Examples of vehicles which may be employed include ricinoleates, such as castor oil as disclosed in U.S. Pat. No. 4,408,310, polyol vehicles, such as polyethylene glycol and/or propylene glycol as disclosed in U.S. Pat. Nos. 3,892,856 and 3,892,857, and in copending U.S. application Ser. No. 325,708, filed Nov. 30, 1981, all of the above being incorporated herein by reference.

The cream or lotion will also contain antioxidants, emulsifier-thickeners, preservatives and anti-foaming-anti-whitening agents and other conventional cream or lotion ingredients, examples of which are disclosed in U.S. Pat. Nos. 3,892,856, 3,892,857 and 4,048,310 as well as application Ser. No. 325,708 referred to above.

The steroid monohydrates of the invention are physiologically active substances which possess glucocorticoid and antiinflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroid monohydrate of this invention can be used topically in lieu of known glucocorticoids in the treatment of skin conditions such as dermatitis, psoriasis, sunburn, neurodermatitis, eczema, and anogenital pruritus.

When given orally, the compounds of this invention may be used in a dosage range of 0.1 to 200 milligrams, preferably 0.3 to 100 milligrams. If administered topically, the compounds of this invention may be used in the range of 0.01 to 5.0% by weight, preferably 0.05 to 2.0% by weight, in a conventional cream or lotion.

The following Examples represent preferred embodiments of the invention. All temperatures are expressed in degrees Centigrade.

EXAMPLE 1

Preparation of monohydrate of 21-(acetyloxy)-9-fluoro-1',2',3',4'-tetrahydro-11β-hydroxypregna-1,4-dieno[16α,17-b]naphthalene-3,20-dione having stable particle size 21-[Acetyloxy]-9-fluoro-1',2',3',4'-tetrahydro-11β-hydroxypregna-1,4-dieno[16α,17-b]naphthalene-3,20-dione (60 gm) was run through a Trost Mill Model Gem-T (Garlock, Newton, Pa.) micronizing machine to reduce average particle size to less than about 4 microns, that is 2–3 microns.

In order to establish that the above steroid undergoes formation of the monohydrate with concomitant crystal growth when introduced into water, the following experiments were carried out.

A. A portion of the micronized anhydrous steroid (2–3 micron particle size) was suspended in water and upon examination after an hour, the particle size distribution changed dramatically to long thin needles about 50 microns in length. Upon TGA (thermal gravimetric analysis) analysis and Karl-Fischer analysis of water content, it was determined that a monohydrate of the steroid formed in solution. It was also found that polysorbate 60, either used to wet the micronized steroid first or added to the suspension afterwards, facilitated hydrate formation while producing crystals exhibiting increased geometric symmetry.

B. A portion of the micronized anhydrous steroid was incorporated into a cream formulation (10% steroid) and after about 4 hours, it was observed that a significant portion of the steroid was converted to the monohydrate with concomitant crystal growth in the cream itself.

C. In accordance with the invention, a monohydrate of the above steroid having a stable average particle size of less than 10 microns was prepared as described below.

50 mg. of micronized steroid (as described above) was wetted by 3 ml of 0.5% polysorbate 60 and then added to 500 ml of water. The resulting aqueous suspension was recycled through a Manton-Gaulin Homogenizer under 6000 psi pressure for about 5 minutes. Microscopic examination of the resulting suspension, immediately and 5 days later, showed no particles larger than 10 microns and the majority was less than 5 microns in size. Before comminution, the micronized steroid had formed a monohydrate characterized by needle-like crystals about 50 to 75 microns in length.

EXAMPLE 2

A steroid cream of the following composition is prepared as described below.

| Ingredient | Amount |
| --- | --- |
| Steroid monohydrate prepared as in Example 1 in 10% aqueous suspension (average particle size less than 10 microns) | 0.1 gm |
| Polysorbate 60 | 8 gm |
| Cetyl alcohol | 10 gm |
| Myristyl stearate | 5 gm |
| Isopropyl palmitate | 10 gm |
| Methyl paraben | 0.2 gm |
| Water q.s. | 100 gm |

(1) The cetyl alcohol, myristyl stearate and isopropyl palmitate and polysorbate 60 are heated to about 90° C. and melted.

(2) Add appropriate amount water to the mixture of (1), stir well, allow to cool down to 30°-40° C. gradually (3) Use a small amount of water and polysorbate to wet the steroid monohydrate to form a smooth paste.

(4) Add the steroid to the cream base prepared under (2)

The above cream has excellent size stability even after prolonged storage.

EXAMPLE 3

A liter of lotion of the following composition is prepared as described below.

| Ingredient | Amount |
| --- | --- |
| Steroid monohydrate of Example 1 (if 10% aqueous suspension was used, need 10 ml) | 1 gm |
| Cetyl alcohol | 32 gm |
| Stearyl alcohol | 21 gm |
| Polysorbate 20 | 23 gm |
| Sorbitan monopalmitate | 53 gm |
| Antifoam A silicon | 0.1 gm |
| Propylene glycol | 150 gm |
| Water q.s. to make | 1 liter |

(1) The cetyl alcohol, stearyl alcohol, polysorbate 20 and sorbitan monopalmitate are heated to about 85° C. and melted.

(2) A portion of the propylene glycol is added to the water and the solution is heated to about 85° C.

(3) Mixtures (1) and (2) are combined at about 85° C., the Antifoam A Silicone is added, and the mixture is stirred rapidly at 85° C. to form a lotion, which is cooled to room temperature.

(4) The steroid monohydrate is dispersed into the remaining propylene glycol and blended with the lotion vehicle from (3) at room temperature.

The steroid monohydrate is found to retain its particle size stability even upon prolonged storage.

EXAMPLES 4 TO 7

A steroid monohydrate cream formulation having a stable particle size and the composition set out below is prepared as follows.

| % by weight Steroid Monohydrate | Example 4 0.2%, | Example 5 0.1%, | Example 6 0.05%, | Example 7 0.025%, |
| --- | --- | --- | --- | --- |
| | per 100 gm | | | |
| Steroid monohydrate of Example 1 (average particle size less than 10 microns) | 0.2 g | 0.1 g | 0.05 g | 0.025 g |
| Glyceryl Stearates | 7.0 g | 7.0 g | 7.0 g | 7.0 g |
| Cetyl Alcohol, N.F. | 5.0 g | 5.0 g | 5.0 g | 5.0 g |
| White Wax, USP | 3.0 g | 3.0 g | 3.0 g | 3.0 g |
| Isopropyl Palmitate | 3.0 g | 3.0 g | 3.0 g | 3.0 g |
| Tween 60 | 4.0 g | 4.0 g | 4.0 g | 4.0 g |
| Propylene Glycol, USP | 15.0 g | 15.0 g | 15.0 g | 15.0 g |
| Dimethicone 350 | 1.0 g | 1.0 g | 1.0 g | 1.0 g |
| Citric Acid Anhydrous, USP | 0.02 g | 0.02 g | 0.02 g | 0.02 g |
| Purified Water, USP To make | 100 g | 100 g | 100 g | 100 g |

The 0.2% potency formulation is prepared as follows:

1. In a suitable stainless steel or glass lined container the glyceryl stearates, cetyl alcohol, white wax and isopropyl palmitate are heated and melted at 90°-95° C. and mixed until homogeneous.

2. In a separate stainless steel or glass lined container the citric acid, tween 60, and a portion of the propylene glycol in the purified water are added, heated to 90°-95° C. and stirred until all solids are dissolved.

The hot oil phase in Step No. 1 is added to the hot aqueous phase in Step No. 2 and agitation is continued for ca 30 minutes while maintaining the mixture at 90°-95° C.

The Dimethicone 350 (silicone DC 200 fluid) is added to the batch with continuous agitation and the batch is then cooled to ca 25°-28° C. In a separate container steroid monohydrate is dispersed in the remaining portion of the propylene glycol. The dispersion is agitated or homogenized until smooth. The monohydrate dispersion is added to the main batch of cream base and mixing is continued until homogeneous using slow speed agitation. Sufficient purified water is then added to bring the batch to final weight and the batch is stirred until homogeneous.

Each of the lower potency creams 0.1%, 0.05% and 0.025% are prepared by dilution of the 0.2% cream with similar cream containing no steroid. The dilutions are prepared by hand levigation with a spatula on a pill tile using the geometric dilution method.

All of the cream formulations of Examples 4 to 7 are found to have excellent particle size stability.

EXAMPLE 8

In a manner similar to that described in Example 1, a monohydrate of (11$\beta$,16$\beta$)-9-fluoro-1',2',3',4'-tetrahydro-11,21-dihydroxypregna-1,4-dieno[16,17-b]naphthalene-3,20-dione is formed having an average stable particle size of less than 10 microns.

EXAMPLE 9

A cream formulation is prepared as described in Example 2 except that the monohydrate of Example 8 is employed in place of the Example 1 monohydrate.

The so-formed cream formulation has excellent steroid particle size stability.

EXAMPLE 10

A lotion formulation is prepared as described in Example 3 except that the monohydrate of Example 8 is employed in place of the Example 1 monohydrate.

The so-formed lotion has excellent steroid particle size stability.

EXAMPLES 11 TO 14

A steroid monohydrate cream formulation having a stable particle size and the composition set out below is prepared as described in Examples 4-7.

| % by weight<br>Steroid Monohydrate | Example 11<br>0.2%, | Example 12<br>0.1%, | Example 13<br>0.05%, | Example 14<br>0.025%, |
|---|---|---|---|---|
| | per 100 gm | | | |
| Steroid monohydrate of Example 8 (average particle size less than 10 microns) | 0.2 g | 0.1 g | 0.05 g | 0.025 g |
| Glyceryl Stearates | 7.0 g | 7.0 g | 7.0 g | 7.0 g |
| Cetyl Alcohol, N.F. | 5.0 g | 5.0 g | 5.0 g | 5.0 g |
| White Wax, USP | 3.0 g | 3.0 g | 3.0 g | 3.0 g |
| Isopropyl Palmitate | 3.0 g | 3.0 g | 3.0 g | 3.0 g |
| Tween 60 | 4.0 g | 4.0 g | 4.0 g | 4.0 g |
| Propylene Glycol, USP | 15.0 g | 15.0 g | 15.0 g | 15.0 g |
| Dimethicone 350 | 1.0 g | 1.0 g | 1.0 g | 1.0 g |
| Citric Acid Anhydrous, USP | 0.02 g | 0.02 g | 0.02 g | 0.02 g |
| Purified Water, USP To make | 100 g | 100 g | 100 g | 100 g |

What is claimed is:

1. A method for forming the monohydrate of a steroid, said monohydrate having an average particle size of less than about 20 microns, said steroid having the structure

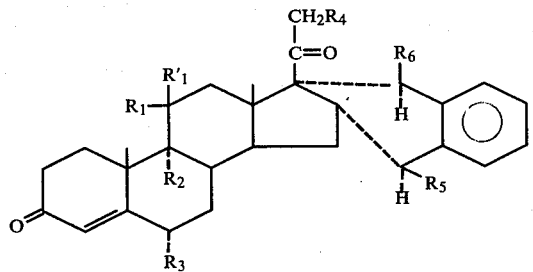

wherein $R_1$ is chlorine, fluorine or hydroxy and $R'_1$ is hydrogen or $R_1$ and $R'_1$ together are =O; $R_2$ is hydrogen or halogen; $R_3$ is hydrogen, methyl or fluorine; $R_4$ is hydrogen, hydroxy,

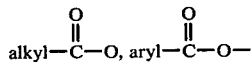

or halogen; and $R_5$ and $R_6$ are the same or different and are hydrogen, alkyl, alkylthio, alkoxy, carboalkoxy, formyl,

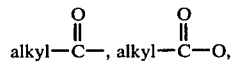

hydroxy, halogen, phenyl or cyano, with the proviso that when $R_5$ and $R_6$ are different, one of $R_5$ and $R_6$ is hydrogen, which method includes the steps of micronizing the steroid in anhydrous form, introducing the micronized anhydrous steroid into water to hydrate the steroid to form the corresponding monohydrate and cause crystal growth, reducing the average particle size of the crystals of hydrated steroid suspended in water to below about 25 microns to form particles of steroid monohydrate having a relatively stable crystal size.

2. The method as defined in claim 1 wherein the average particle size of the crystals of hydrated steroid is in the range of from about 40 to 90 microns and is reduced to an average particle size of less than about 20 microns.

3. The method as defined in claim 1 wherein crystals of hydrated steroid are reduced to an average particle size of less than about 10 microns.

4. The method as defined in claim 3 wherein crystals of hydrated steroid are reduced to an average particle size of less than about 5 microns.

5. The method as defined in claim 1 wherein the anhydrous steroid is 21-(acetyloxy)-9-fluoro-1',2',3',4'-tetrahydro-11β-hydroxypregna-1,4-dieno[16α,17-b]naphthalene-3,20-dione.

6. The method as defined in claim 1 wherein the anhydrous steroid is (11β,16β)-9-fluoro-1',2',3',4'-tetrahydro-11,21-dihydroxypregna-1,4-dieno-[16,17-b]naphthalene-3,20-dione.

7. The method as defined in claim 1 wherein the micronized anhydrous steroid is allowed to remain in the water for a period of from about 0.1 to about 4 hours to allow for formation of a monohydrate and crystal growth.

8. The method as defined in claim 1 wherein the water and micronized anhydrous steroid form a suspension containing from about 5 to about 20% steroid.

9. The method as defined in claim 1 wherein the steroid in anhydrous form is micronized to an average particle size of below about 5 microns.

10. A method for forming the monohydrate of a steroid, said monohydrate having an average particle size of less than 20 microns, said steroid having the structure

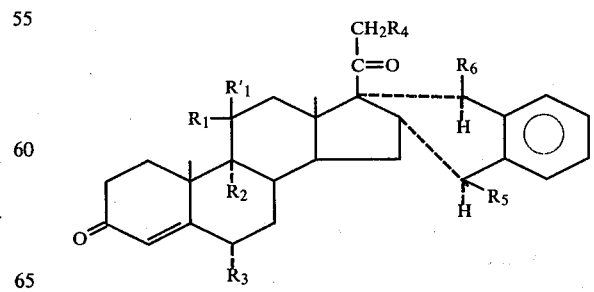

wherein $R_1$ is chlorine, fluorine or hydroxy and $R'_1$ is hydrogen or $R_1$ and $R'_1$ together are =O, $R_2$ is hydrogen or halogen; R₃ is hydrogen, methyl or fluorine; R₄ is hydrogen, hydroxy,

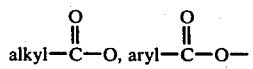

or halogen; and R₅ and R₆ are the same or different and are hydrogen, alkyl, alkylthio, alkoxy, carboalkoxy, formyl,

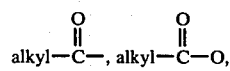

hydroxy, halogen, phenyl or cyano, with the proviso that when R₅ and R₆ are different, one of R₅ and R₆ is hydrogen, which method includes the steps of micronizing the steroid in anhydrous form and subjecting the micronized anhydrous steroid to a relative humidity of higher than 40% for a period of at least about 4 hours to form a monohydrate of the steroid while controlling and limiting crystal size of the steroid monohydrate.

11. The method as defined in claim 10 wherein the anhydrous steroid is micronized to an average particle size of 10 microns or less.

12. The method as defined in claim 10 wherein the steroid monohydrate has a stable average particle size of 5 microns or less.

13. The method as defined in claim 10 wherein the micronized anhydrous steroid is in the form of a thin layer as it is subjected to the high relative humidity.

14. The method as defined in claim 11 wherein the micronized anhydrous steroid is subjected to the high relative humidity for a minimal period of about one day.

* * * * *

UNITED STATES PATENT AND TRADEMARK OFFICE
CERTIFICATE OF CORRECTION

PATENT NO. : 4,391,755
DATED : July 5, 1983
INVENTOR(S) : Yu-Chang J. Wang et al.

It is certified that error appears in the above—identified patent and that said Letters Patent is hereby corrected as shown below:

On the title page, the second inventor should be
--Friedrich Dürsch--.
In the abstract, the structure should read -- 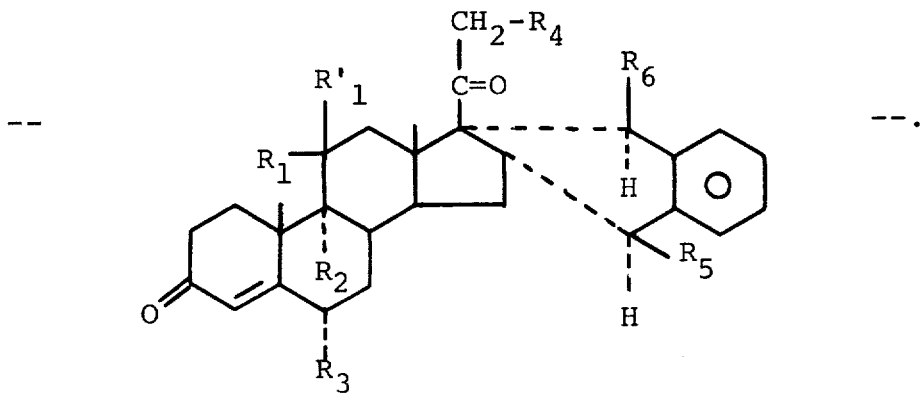 --.

Column 3, line 1, "for" should read --from--.

Signed and Sealed this

Twenty-fourth Day of April 1984

[SEAL]

Attest:

GERALD J. MOSSINGHOFF

Attesting Officer    Commissioner of Patents and Trademarks